United States Patent [19]

Haseltine et al.

[11] Patent Number: 4,981,790
[45] Date of Patent: Jan. 1, 1991

[54] STABLE TATIII CELL LINES, TATIII GENE PRODUCTS, AND ASSAY METHODS

[75] Inventors: William A. Haseltine, Cambridge; Craig A. Rosen, Brookline; Joseph G. Sodroski, Cambridge; Wei C. Goh, Somerville, all of Mass.

[73] Assignee: Dana Farber Cancer Institute, Boston, Mass.

[21] Appl. No.: 806,263

[22] Filed: Dec. 6, 1985

Related U.S. Application Data

[63] Continuation-in-part of Ser. No. 614,297, May 25, 1984.

[30] Foreign Application Priority Data

May 24, 1985 [CA] Canada ............................. 482374
May 24, 1985 [WO] PCT Int'l Appl.. PCT/US85/00985

[51] Int. Cl.$^5$ ..................... C12P 21/00; C12N 15/00; C12N 5/00
[52] U.S. Cl. ........................... 435/69.1; 435/172.3; 435/240.2; 435/320; 536/27; 935/1; 935/34; 935/41; 935/70; 935/32
[58] Field of Search ............... 435/68, 70, 172.3, 135, 435/240, 247, 257, 317, 69.1, 240.2, 172.3, 320; 536/29, 27; 935/19, 32, 34, 39, 87

[56] References Cited

PUBLICATIONS

Sodroski et al., (1985), (a) Science, 229:74–77.
Sodroski et al., (1984), (b) Science, 225:381.
Sodroski et al., (1985), (c) Science, 227:171.
Arya et al., (1985), Science, 229:69–73.
Hahn et al., (1984), Nature, 312:166–8.
Marx, Science, 224:475–477, 1984.
Gaynor, Richard et al., Proc. Natl. Acad. Sci. U.S.A., 81:1193–1197, (2/84).
F. Barre-Sinoussi et al., Science, 200:868, (1983).
R. C. Gallo et al., ibid, 224:500, (1984).

(List continued on next page.)

Primary Examiner—Robin L. Teskin
Assistant Examiner—Beth A. Burrous
Attorney, Agent, or Firm—David G. Conlin; Ronald I. Eisenstein

[57] ABSTRACT

This invention describes stable tat$_{III}$ cell lines. It is disclosed that by transfecting a preselected tat$_{III}$ cell line with a vector containing a sufficient amount of the HTLV-III LTR responsive to tat$_{III}$ gene products for trans-activation and an enhancer upstream of the tat$_{III}$ responsive segment, it is possible to express high levels of the tat$_{III}$ gene products. By including a preselected heterologous gene on this vector, it is also possible to express high levels of a desired gene product. A substantially pure protein comprising 86 amino acids and having an apparent molecular weight of about 14,000 dalton and exhibiting trans-activating activity is also disclosed. This protein and polypeptides having trans-activating ability, which is also disclosed, can be used to produce high levels of a desired gene product. A method of detecting the presence of HTLV-III/LAV virus in an individual is also disclosed and comprises the step of:

(a) incubating whole blood or lymphocytes from the invididual to be tested with tat$_{III}$ cell lines of the present invention in a culture medium; and
(b) screening for cytopathic effects on the cells is also disclosed. A method of screening for a compound that inhibits trans-activation of the tat$_{III}$ gene product is also disclosed and comprises the steps of:
 (1) transacting a tat$_{III}$ cell line of the present invention with a vector containing a gene that expresses a selectable marker and whose expression is under the control of an HTLV-III LTR;
 (2) transfecting the same type of tat$_{III}$ cell lines as in step (1) with the selectable gene chosen in step (1) but under the control of a different regulatory sequence;
 (3) thereafter, adding a preselected compound to each of the cell lines in increasing concentrations; and
 (4) measuring the expression of the selectable gene product to determine whether the compound effects the tat$_{III}$ function without being toxic to the cell.

16 Claims, 7 Drawing Sheets

OTHER PUBLICATIONS

J. Schupback et al., ibid, 503.
Sarngadharan et al., ibid. 506.
J. A. Levy et al., ibid, 225,840, (1984).
D. Klatzmann et al., Nature, (London), 312:767, (1984).
M. Gottlieb et al., N.E. J. Med., 305:1425, (1981).
H. Masur et al., ibid, 1431.
F. Siegal et al., ibid, 1439.
H. Lane et al., ibid, 309, 453, (1983).
J. Ziegler et al., ibid, 311,565, (1984).
G. Shaw et al., Science, 227:177, (1985).
D. Klatzmann et al., Science, 225:54, (1984).
M. Seligman et al., N.E. J. Med., 311:1286, (1984).
M. Popovic et al., Science, 224:497, (1984).
Sodroski et al., Science, 119, 74, (1985).
Cepko et al., Cell, 37:1053–1062, (1984).
Southern P. J. et al., J. Mol. Appl. Genet., 1:327–341, (1982).
Wigler et al., Cell, 16, 777–785, (1979).
Cone et al., PNAS, 81:6349–6353, (1984).
Mann et al., Cell, 33:153–159, (1983).
King et al., Science, 228:554–558, (1985).
G. Weinstock et al., PNAS, 80,4432, (1983).

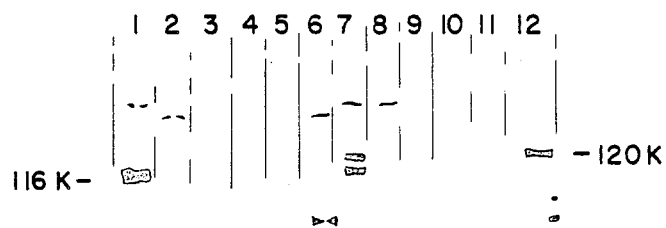
FIG.6A
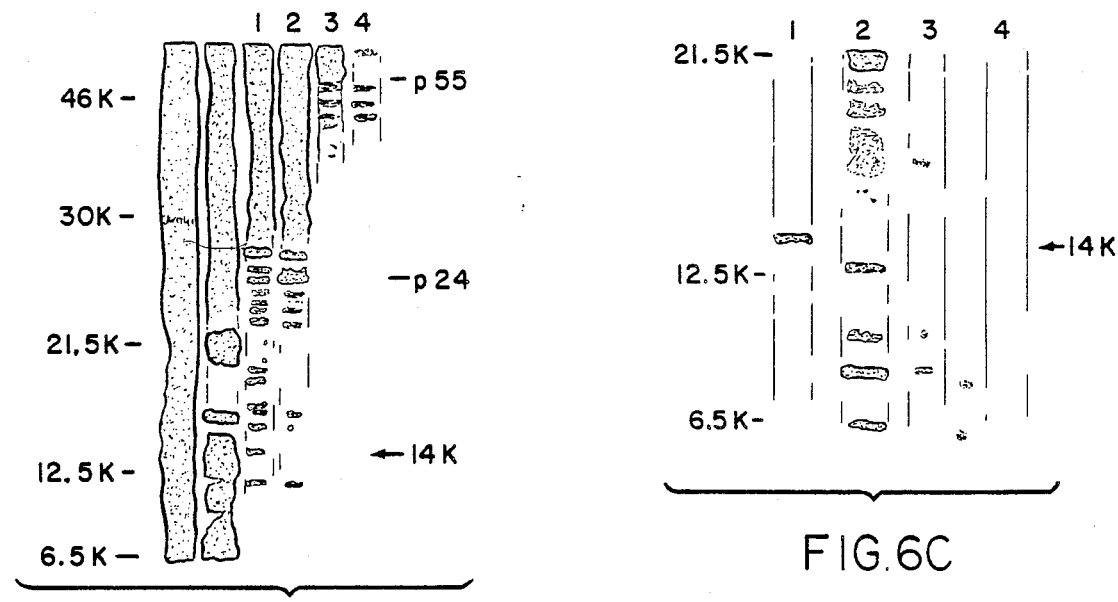
FIG.6B
FIG.6C
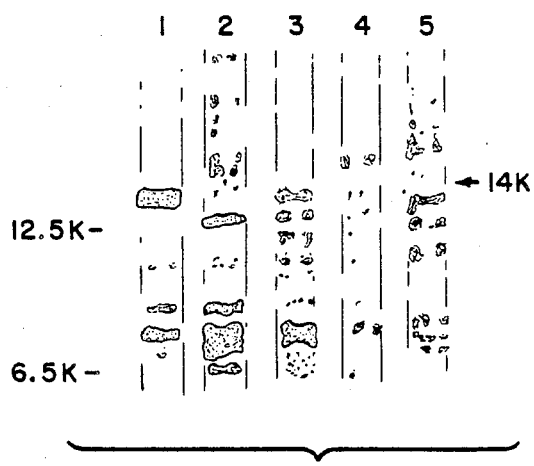
FIG.6D
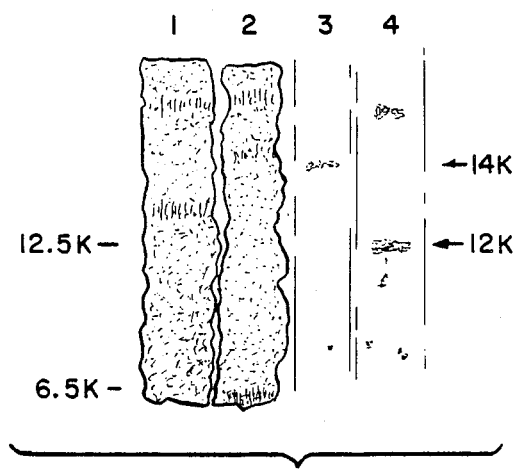
FIG.6E

FIG. 7-2

STABLE TATIII CELL LINES, TATIII GENE PRODUCTS, AND ASSAY METHODS

This is a continuation-in-part of co-pending U.S. patent application Ser. No. 614,297, filed May 25, 1984.

The present invention is directed to the establishment of cell lines that stably express the $tat_{III}$ gene, and the use of the gene product. More particularly a protein and a polypeptide are described which can dramatically increase the rate of expression of a heterologous gene product.

Much effort has been spent over the years in attempting to understand the mode of action of viruses, particularly that of retroviruses. Questions for which answers have been sought include the reasons that certain of these viruses preferentially infect and/or replicate in certain types of cells as opposed to other types of cells.

The acquired immune deficiency disease (AIDS), and AIDS-related complex are the subjects of intensive scientific research and public concern. Human T-Cell leukemia virus III (HTLV-III)/LAV is the etiological agent of the acquired immune deficiency disease, AIDS-related complex and other virus-related disorders including degeneration of the central nervous system, lymphoid interstital pneumonitis (LIP) an increased incidence of Kaposi's sarcoma, B-cell lymphoma of a Burkitt's type, Hodgkin's lymphoma and thrombocytopenic purpera, collectively called HTLV-III/LAV related disorders [F. Barre'-Sinoussi et al., Science 200:868 (1983): R. C. Gallo et al., ibid., 224:500 (1984); J. Schupback et al., ibid.: 503; M. G. Sarngadharan et al., ibid.: 506; J. A. Levy et al., ibid.: 225,840 (1984); D. Klatzmann et al., Nature (London) 313:767 (1984); M. Gottlieb et al., New England J. Med. 305:1425 (1981); H. Masur et al., ibid.: 1431; F. Siegal et al., ibid.: 1439; H. Lane et al., ibid.: 309,453 (1983); J. Ziegler et al., ibid.: 311,565 (1984); G. Shaw et al., Science 27:177 (1985). D. Klatzman et al., Science 225:54 (1984); M. Seligman et al., New England J. Med. 311:1286 (1984).] AIDS is clinically typified by depletion of T-Cells of the T4+(helper) subset, a phenomena reflected by cytotoxicity of the virus for T4+ cells in vitro. Large scale production of the virus was made possible by the development of T4+ cell lines that were susceptible to virus infection but that were partially resistant to its cytopathic effects [M. Popovic et al., Science 224:497 (1984).]

We have previously discovered genes in HTLV-I, HTLV-II, and HTLV-III, which code for proteins resulting in trans-activation of their respective viruses. (See PCT/US85/00985 filed May 24, 1985 which is incorporated herein by reference). These genes have been previously referred to as x-lor genes as well as luk genes, but have been collectively re-named tat genes using the conventional method of naming genes by function.

Being able to establish cell lines that stably express the $tat_{III}$ gene without the possibility of virus spread provides an opportunity to study the biochemical events associated with $tat_{III}$ gene expression in vivo, as well as obtaining large scale quantities of the $tat_{III}$ gene products, and/or a desired heterologous gene product.

SUMMARY OF THE INVENTION

We have now discovered a method for producing cell lines that will stably express the $tat_{III}$ gene in vitro using defective HTLV-III/LAV virus, thus eliminating the possibility of virus spread in the absence of helper virus. These $tat_{III}$ cell lines can be used to express a large quantity of a desired gene product.

In addition, we have discovered a protein of approximately 14,000 daltons consisting of 86 amino acids, which is the functional $tat_{III}$ protein. A polypeptide weighing only approximately 12,000 daltons molecular weight, containing the first 69 amino acids of the $tat_{III}$ protein will also provide activity similar to that of the $tat_{III}$ protein.

The $tat_{III}$ cell line and/or the gene product can be used in the production of large quantities of a desired product from a chosen tissue by using a modified LTR vector containing a desired heterologous gene product. The $tat_{III}$ cell lines of the present invention can also be used for assay purposes. These cells can be used to detect the presence of HTLV-III/LAV virus in individuals more easily and with greater sensitivity than current diagnostic methods.

Additionally, these cell lines can be used to screen for compounds that inhibit the trans-activation of the $tat_{III}$ gene product. This method includes the steps of:

(a) transfecting a $tat_{III}$ cell line with a vector containing a gene that expresses a selectable marker and whose expression is under the control of an HTLV-III LTR;

(b) transfecting the same type of $tat_{III}$ cell line as in step (a) with the selectable gene chosen in step (a) but under the control of a different regulatory sequence;

(c) thereafter adding a preselected compound to each of the cell lines in increasing concentrations; and (d) measuring the expression of the selectable gene product to determine whether the compound effects the $tat_{III}$ function without being toxic to the cell.

BRIEF DESCRIPTION OF THE FIGURES

FIG. 6 A-E illustrates the expression of fusion proteins that contain the $tat_{III}$ protein.

DETAILED DESCRIPTION OF THE INVENTION

The present invention is directed to the establishment of stable cell lines which express the $tat_{III}$ gene. We have found that the prolific replication of the HTLV-III/LAV is in part caused by the presence of the $tat_{III}$ gene. This gene regulates gene expression directed by the HTLV-III/LAV long terminal repeat (LTR) sequence (Sodroski et al., Science 227:171 (1985); Sodrosk et al., ibid., 119,74 (1985); S. Arya et al., ibid., 69 (1985)). Because these $tat_{III}$ do not contain the complete HTLV-III/LAV genome, it is possible to study the biochemical events associated with the $tat_{III}$ gene without the possibility of virus spread.

We have discovered that cell lines which stably express the tat$_{III}$ gene can be created by infection using a vector modified from the retroviral infector pZIPNEO (Cepko et al., *Cell* 37: 1053-1062 (1984).

The vectors used in the present invention can be in the form of plasmids or viral vectors such as those described in PCT/US85/00986 filed May 24, 1984. For example, the defective retroviral vector pZIP-NEOSV(X)1 prepared as described by Cepko et al., supra contains Moloney murine leukemia virus LTR's, polyadenylation signals, sequences required for reverse transcription and for encapsidation of RNA, as well as the 5' and 3' splicing signals that normally produce subgenomic env gene messenger RNA. This vector also contains the bacterial gene for neomycin resistance (neo) which confers a dominant selectable resistance to the antibiotic G418 in eukaryotic cells (Southern, P. J. et al., *J. Mol. Appl. Genet.* 1:327-341 (1982) so that tat$_{III}$ transfected cells identified. However, any indicator which can be identified can be used in a tat$_{III}$ vector.

Figure 1:
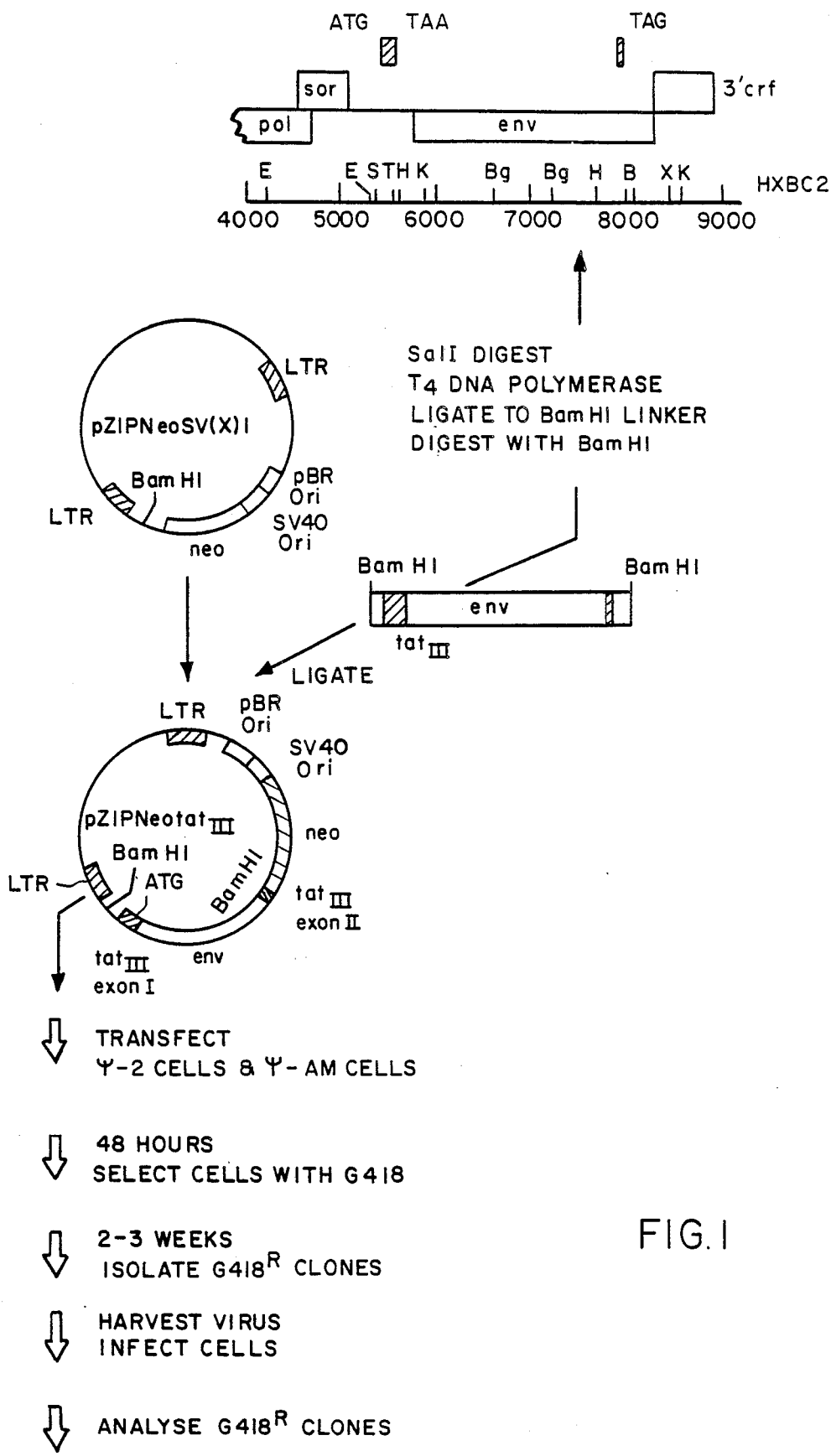
FIG. 1 illustrates a method according to the present invention of establishing a cell line containing the $tat_{III}$ gene.

The HTLV-III/LAC tat$_{III}$ gene was obtained from infectious proviral clone HXBC2 and encodes the HTLV-III/LAV associated trans-acting factor (See FIG. 1) (Arya et al., *Science* 229: 69-73 (1985); Sodroski et al., *Science* 229:74-77 (1985)) This vector was prepared as described in FIG. 1.

DNA was introduced into the psi/2 (ecotropic) and psi AM (amphotropic) cell lines by the calcium phosphate coprecipitation method (Wigler et al., *Cell* 16:777-785 (1979). These lines constitutively produce the murine leukemia virus proteins but cannot package the viral transcripts (Cone, at el., *PNAS* 81: 6349-6353 (1984); Mann, et al., *Cell* 33:153-159 (1983)). Two days following transfection, cells were selected with the antibiotic G418 (400 μg/ml for fibroblast lines and 700 μg/ml for lymphocytes). G418 resistant clones were evident in 7 to 10 days. Insertion of the tat regions does not interfere with splicing events required for transcription of the neo genes. G418-resistant psi 2 and psi AM clones were isolated and the virus from clones producing greater than 10$^3$ infectious units per ml were used to infect the test cells. (King et al., *Science* 228:554-558 (1985)). Cells resistance to G418 were observed subsequent to infection of all the cell lines tested.

We have found that by substituting the Moloney LTR with other modified LTR's a tissue specific expression vector can be obtained. The vectors are constructed using a tissue specific enhancer(s) operatively positioned in the same sequence with a heterologous DNA segment corresponding to the polypeptide of interest, as well as a stop codon and polyadenylation sequence downstream (3') from that gene. The vector should also contain a replication origin.

The vector contains at least the segment of an enhancer which determines the tissue specificity of that enhancer, hereinafter referred to as the "tissue specificity determinant." The vector preferably contains a complete viral enhancer, rather than just the tissue specific determinant from such an enhancer and preferably the tissue specific determinant is part of the complete enhancers.

The promoter contained in the vector can be any of the known promoters which function to permit expression of a desired product in the host of choice. Preferably the promoter is a viral promoter from the same class of virus as the enhancer. The preferred class of virus is retrovirus, and the preferred viruses for use in conjunction with the invention are the Akv, SL3-3, and Friend viruses.

The term "tissue specific" as used in this disclosure and claims, means that the vector operates to produce a greater amount of desired product in the targeted tissue than it does in other tissues under normal culture conditions. Tissue specific vectors may produce 1.5 to 1,000 or more times as much expression product in the target tissue as in other tissues. These tissue specific expression vectors are more fully described in PCT/US85/00986 which is incorporated by reference.

The tissue specific determinant can bed homologous, meaning it came from the same virus as the promoter, or heterologous, in which case it is not from the same virus as the promoter. Heterologous tissue specific determinants can be excised from other viral systems, or can be synthesized using known techniques. Tissue specific determinants which are specific to the target tissue can be identified by assay techniques, where vectors encoding an indicator or marker compound, e.g., chloramphenicol acetyl transferase (CAT), an indicator which can be easily quantified as described below, to determine which vectors are effective in the tissue.

If desired, enhancer(s) from tissue specific vectors can be compared in DNA sequence to the enhancers which are not specific to the target tissue to determine the DNA sequence of the tissue specific determinant. Thereafter, at least the tissue specific determinant, preferably the entire enhancer, may be utilized in the desired vector containing the tat$_{III}$ gene and the resulting tissue specific vectors utilized to express this gene product in the tissue of choice.

Various cell lines differ in their ability take up and express the transfected "tat$_{III}$" DNA. We have found that Raji cells, HUT 78 cells, Jurkat cells, HeLa cells and NIH 3T3 cells are useful. Human T-cells and B-cells, generally are very useful. Another useful method of achieving transfection with the "tat$_{III}$" DNA is to use cells infected with either HTLV-I or HTLV-II.

Figure 2A:
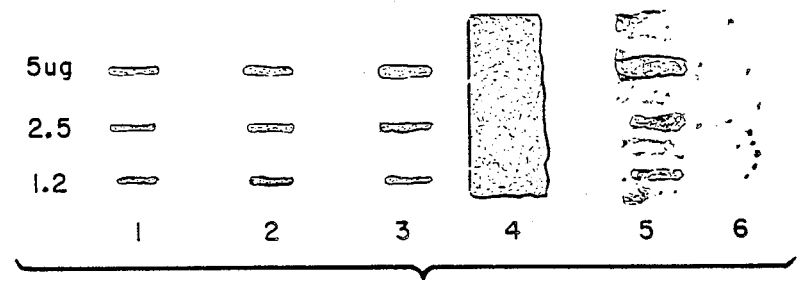
FIG. 2 illustrates the dramatic difference in the CAT activity seen in infected vs. uninfected cells.

To test for the presence of tat$_{III}$ gene transcripts, the total cellular RNA was extracted from several clonal isolates of infected NIH 3T3 and HeLa cells. FIG. 2A demonstrates that tat$_{III}$ gene transcripts were present in the respective infected cells and absent from uninfected controls. This demonstrates that it is possible for the tat$_{III}$ gene and the neo gene to be transcribed by use of these vectors.

Figure 3:
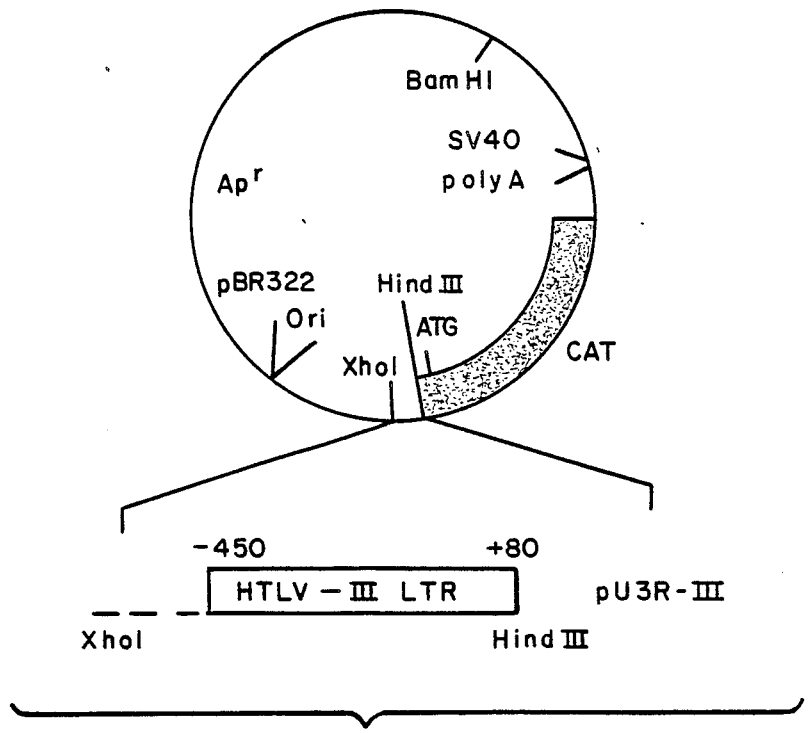
FIG. 3 illustrates the plasmid used to assess the trans-activation.

To determine whether the tat$_{III}$ gene is functional, the tat$_{III}$ cell lines of the present invention were transfected with plasmid pU3R-III (FIG. 3). This plasmid contains HTLV-III/LAV LTR sequences 5' to the CAT gene (See U.S. patent application Ser. No. 614,297). In PCT/US 85/00985 filed May 24, 1985,we demonstrated that the tat$_{III}$ gene product activates in trans gene expression directed by the HTLV-III/LAV LTR.

Figure 2B:
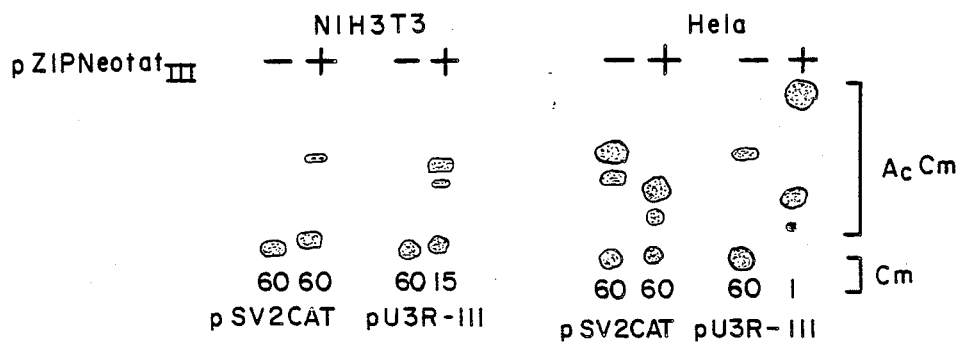

The level of HTLV-III/LAV LTR directed gene expression was dramatically increased in ZIPNeotatIII-infected HeLa cells compared with uninfected cells as shown in FIG. 2B. See also Table 1. For example relative to pSV2CAT, gene expression directed by plasmid pU3R-III, was increased between 760 and 1100 times depending upon the clone tested. In ZIPNeotatIII-infected Raji cells, HTLV-III/LAV LTR-directed gene expression was increased approximately 2000-fold relative to the control of uninfected Raji cells. The level of CAT activity was increased by 6.5 to 23 times in infected NIH 3T3 cells. The levels of Rous sarcoma virus LTR-and HTLV-I LTR-directed CAT gene expression were the same in infected and in uninfected cells.

Figures 1, 7:
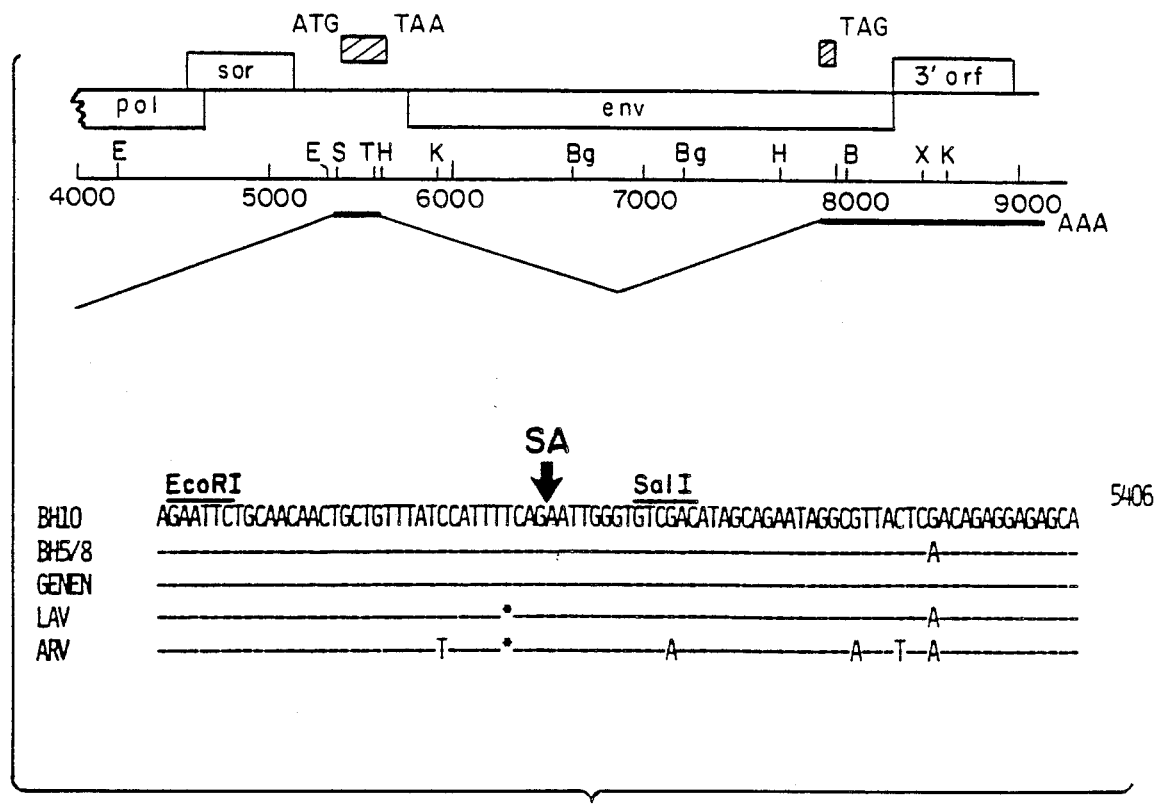
FIG. 7 represents the nucleic acid sequence of the $tat_{III}$ gene and the predicted amino acid sequence.

The first coding exon of the HTLV-III/LAV transactivator gene is shown in FIG. 7. It lies 5' to the envelope gene (from nucleotide 5365 to 5607). A single

TABLE 1

Effect of ZIPNeotatIII infection on HTLV LTR-directed gene expression.

| Virus | Cell Line[b] | Plasmid Relative CAT Activity[a] | | | | |
|---|---|---|---|---|---|---|
| | | pSV2CAT | pU3R-I Stimulation[c] | pU3R-II Stimulation[c] | pU3R-III Stimulation[c] | RSVCAT |
| None | Raji | 1.00 | 0.62 | | 0.24 | 0.81 |
| ZIPNeotatIII | Raji-P | 1.00 | 0.68 | | 530.00 (2208) | 1.40 |
| ZIPNeotatIII | Raji-C1 | 1.00 | | | 650.00 (2708) | |
| ZIPNeotatIII | Raji-C2 | 1.00 | | | 427.00 (1779) | |
| None | Hela | 1.00 | 0.50 | | 0.12 | 6.00 |
| ZIPNeotatIII | Hela-P | 1.00 | 0.61 | | 115.00 (958) | 3.00 |
| ZIPNeotatIII | Hela-C1 | 1.00 | | | 135.00 (1125) | 8.50 |
| ZIPNeotatIII | Hela-C2 | 1.00 | | | 92.00 (766) | 5.70 |
| ZIPNeotatIII | NIH3T3-P | 1.00 | | | 4.70 (23) | 5.20 |
| ZIPNeotatIII | NIH3T3-C1 | 1.00 | | | 1.30 (6.5) | 4.20 |
| ZIPNeotatIII | NIH3T3-C2 | 1.00 | | | 2.20 (11) | 6.00 |

The presence of functional tat$_{III}$ proteins was determined by measuring the level of HTLV-I(pU3R-Ind HTLV-III/LAV (pU3R-III) LTR-directed CAT gene expression following transfection of the respective infected cells. The levels of CAT activity obtained following transfection of uninfected (−) and infected (+) cells with the control plasmid pSV2CAT are also shown. The autoradiograms of FIG. 2B show the level of enyzme activity present in a typical reaction for the time (numbers underneath CAT assays) indicated. Unreacted chloramphenicol (Cm) and acetylated reaction products (AcCm) are also shown.

These experiments demonstrate that we have established cell lines which will stably express the tat$_{III}$ gene product. Moreover, the level of trans-activation in many of these infected cells approximates the level of transactivation obtained with infection by the actual HTLV-III/LAV virus.

The use of these cell lines, which express high levels of tat$_{III}$ genes, permits the development of high-level gene expression systems. For example, the desired genes under control of the HTLV LTR can be introduced either transiently or stably into the tat$_{III}$ cell lines, which should result in the expression of a large quantity of the desired gene product. Such a system, would be useful for the overproduction of the HTLV-env proteins, which in turn, could be used clinically for diagnostic or prophylactic purposes.

The use of the tat$_{III}$ cell lines of the present invention also permit the large scale production of the tat$_{III}$ protein.

Using these tat$_{III}$ cell lines permits the large scale production of other tat$_{III}$ gene products, as well as the tat$_{III}$ protein.

We have now discovered the tat$_{III}$ protein which is approximately 14,000 daltons molecular weight comprising 86 amino acids and exhibits trans-activating activity. Although the region of the HTLV-III/LAV genome necessary for trans-activation of the HTLV-III/LAV LTR had been determined and shown to contain an open reading frame capable of encoding a protein of 86 amino acids in two exons (FIGS. 4 and 7), the trans-activator protein itself had not been identified until now. The protein we have discovered migrates with an apparent molecular weight of 14 kD, is syntehesized from the HTLV-III/LAV transactivator gene and is immunoreactive in some individuals infected with HTLV-III/LAV.

ATG codon at position 5411 could potentially initiate the transactivator protein, tat$_{III}$. The second coding exon is present in an alternate reading frame within the env gene. Doubly-spliced RNA molecules containing these exons have been detected in virus producing cell lines [J. Sodroski et. al., Science 227:171 (1985); J. Sodroski et.al., ibid.: 119,74 (1985); S. Arya et.al., ibid.: 69 (1985)). [M. Popovic et. al., Science 224:497 (1984)].

Figure 5:
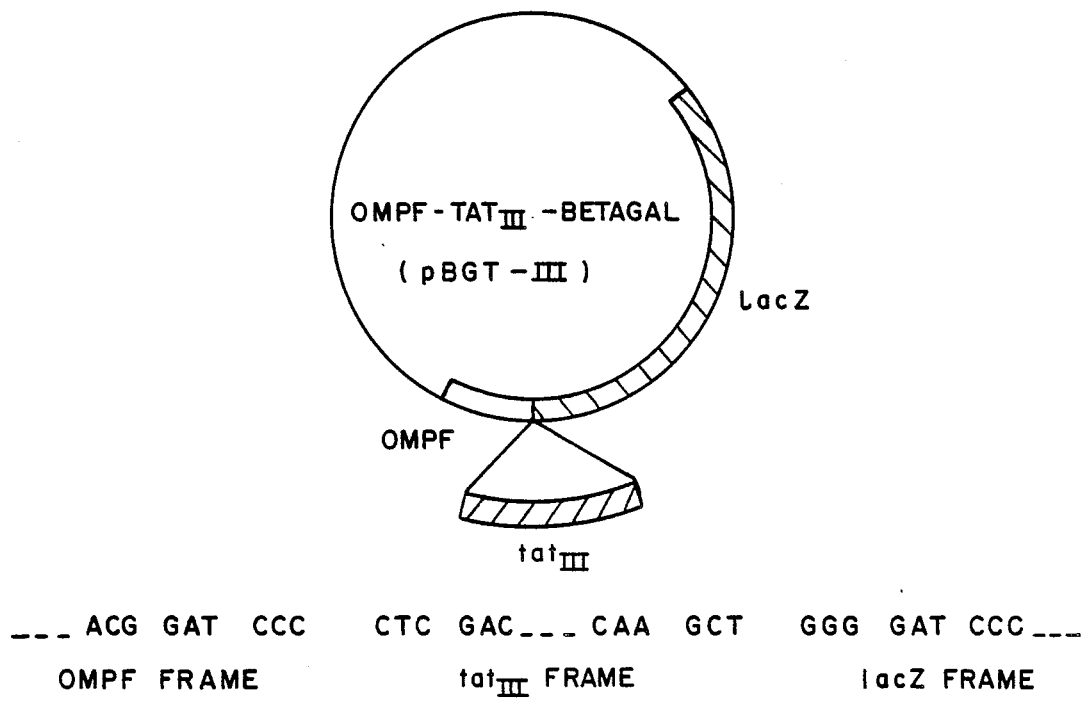
FIG. 5 shows the construction of a $tat_{III}$ fusion product in a bacterial open reading frame infector.

To establish that this open reading frame encodes a functional protein product that is antigenic in patients, 221 nucleotides of the predicted first coding exon from nucleotide 5391 to 5611 were inserted into an open reading frame vector (ORF) containing the bacterial beta-galactosidase gene [G. Weinstock et.al., PNAS 80,4432 (1983)]. Both promoter and translation initiation signals are provided by the ompF gene, an E. Coli gene encoding an abundant outer membrane protein. A plasmid containing the tat$_{III}$ region was constructed so as to create a continuous open reading frame between the ompF and beta-galactosidase genes (ompf-and tat$_{III}$-beta-glactosidase, pBGT-III) (FIG. 5). A plasmid containing an in-frame fusion product between the ompF-beta-galactosidase, genes without an insert was also constructed (ompF-beta-qalactosidase, pBG).

Cells containing the pBGT-III plasmid express an approximately 120 kd fusion protein that can be detected by immunoprecipitation with rabbit anti-beta-galactosidase serum (FIG. 6A). The rabbit anti-beta-galactosidase serum also immunoprecipitates a smaller protein of the expected 116 kd size from cells transformed by the p8G plasmid alone. To determine if the fusion protein is immunogenic in patients, a panel of serum from people seropositive for HTLV-III/LAV was used to immunoprecipitate extracts derived from bacteria containing the plasmids pBG or pBGT-III. Of twenty tested serum samples (five of which are known in FIG. 6A), one was positive (38-1). This serum specifically immunoprecipitated the pBGT-III fusion protein but did not react with the product of the pBG plasmid, indicating that the antigenic determinants recognized by the serum were probably provided by the HTLV-III/LAV insert. This shows that in at least some patients infected with HTLV-III/LAV, the tat-$_{III}$ gene can encode an immunogenic product.

To determine if the positive antiserum, 38-1, could identify a protein encoded by the tat $_{III}$ gene, [$^{35}$S]cysteine labelled whole cell lysates of H9 cells infected with HTLV-III/LAV [(3) Popovic et. al., supra] were used in immunoprecipitation analysis. As a control, a patient serum that was non-reactive with the pBGT-III fusion protein, serum 4-3, was also used. FIG. 6B shows the immunoprecipitation of HTLV-III/LAV infected cells. H9/HTLV-III cells [Popovic et. al., supra] were labelled overnight with 100uCi per ml of [$^{35}$S] cysteine and reacted with a patient antiserum (38-1) that recognizes the ompF-tat$_{III}$-betagal product (lane 1) or a patient antiserum that failed to recognize the ompF-tat$_{III}$-betagal product (4-3). [$^{14}$C] labelled protein markers (Amersham) are shown in the leftmost two lanes, (k=kDa; p, protein; gp, glycoprotein). Both the 38-1 and 4-3 sera recognize the viral envelope glycoproteins gp160/120, the viral gag gene precursor, p55 and smaller viral proteins, including the structural core proteins p24 and p17. However, a 14 kD protein recognized by the 38-1 antiserum is not present in the immunoprecipitates with the 4-3 antiserum and has no reaction. Neither serum immunoprecipitated this protein from uninfected H9 cells. These observations confirm that the 14 kD protein is the product of the bacterial fusion tat$_{III}$ protein.

Figure 4:
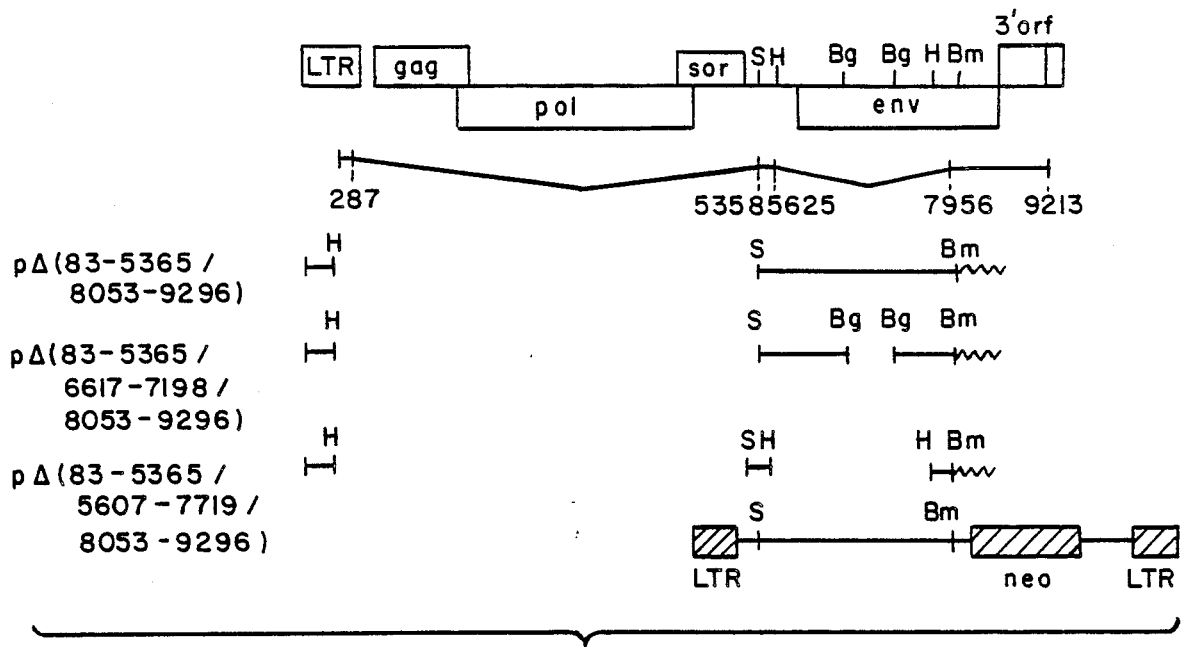
FIG. 4 illustrates the structure of HTLV-III/LAV deletion mutants that retain trans-activating activity.

As further proof that the 14 kD protein is indeed encoded by the trans-activator gene of HTLV,-III/-LAV, it should be present in cells that express only the tat$_{III}$ gene. Thus, HeLa cells were transfected with a deletion mutant of the HTLV-III genome that had previously been designated p Δ83-5365/8053-9296 Δ [Sodroski et. al., supra] (FIG. 4). Cell lines were established by co-transfection with a plasmid that encodes a gene for resistance to the antibiotic G418. This cell line stably expresses the HTLV-III/LAV trans-activator gene as judged by an enhanced rate of HTLV-III/LAV LTR directed expression of the chloramphenicol acetyltransferase (CAT) gene (Table 2). This observation is consistent with previous experiments that show that this plasmid encodes the trans-activating factor.

Immunoprecipitation of the transfected cell line with the 38-1 sera shows a 14 kD protein that is absent in the untransfected Hela cells as shown in FIG. 6C. Clones were selected for resistance to G418. Cells were then labelled overnight with 100uCi of [$^{35}$S]cysteine per ml and total cellular lysates used for immunoprecipitation with either patient anti-serum 38-1 (lane 1) or 4-3 (lane 2) Lanes 3 and 4 are immunoprecipitates of untransfected Hela cells with 38-1 and 4-3 respectively (k=kDa).

The serum 4-3 that does not immunoprecipitate the tat$_{III}$-beta-galactosidase fusion protein also failed to recognize the 14 kD protein. As the plasmid used for transfection had been deleted for all of the gag, pol, sor and 3' ORF coding regions of the HTLV-III/LAV genome, the 14 kD protein cannot be encoded by these regions.

Lymphocytic cell lines were also established by infecting HUT78, a human T-cell line and Raji, a human B-cell line with a retroviral vector, pZIPNeo tat$_{III}$ that was constructed to allow expression of the tat$_{III}$ gene (FIG. 4). The retroviral vector does not contain the gag, pol, sor or 3' ORF open reading frames. In each case, a 14 kD protein that is absent in the respective uninfected parent cell lines is immunoprecipitated with serum 38-1 but not with serum 4-3 (See FIG. 6D). Patient serum 38-1 was used to react with lysates from Raji ZIP tat$_{III}$(lane 1), uninfected Raji cells (lane 2), 2 different clones of HUT78 ZIP tat$_{III}$(lanes 3 and 4) and uninfected HUT78 (lane 5) (k=kDa).

Since a truncated envelope gene is present in the plasmids p Δ(83-5365/8053-9296) and pZIPNeo tat$_{III}$, deletion mutants that had previously been shown to trans-activate the HTLV-III/LAV LTR but do not contain a substantial portion of the env gene were used in transfection assays. Raji cells were transiently transfected with plasmids pΔ(83-5365/8053-9296) ATCC No. 67134 and p Δ(83-5365/6617-7198/8053-9296) which contains a major internal deletion within the env gene (FIG. 4). Immunoprecipitation of cells transiently transfected with both plasmids with serum 38-1 similarly shows a 14 kD protein that is absent in untransfected Raji cells.

Although it is believed that the tat-$_{III}$ gene is encoded by two exons, deletion analysis demonstrated that only the first coding exon is required for tat$_{III}$ activity [Sodroski, supra]. Specifically, a plasmid, pΔ(83-5365/5607-7719/8053-9296), that contains only the first 69 amino acids of the first coding exon and deletes most of the envelope gene was shown to retain tat$_{III}$ activity. (See FIG. 6E). Raji cells were transfected with pΔ(83-5365/8053-9296), pΔ(83-5365/6617-7198/8053-9296) or pΔ(83-5365/5607-7719/8053-9296) using DEAE-dextran as described [Sodroski, supra 8. Queen et al., Cell 33:729 (1983). Cells were harvested after 48 hours and labelled with 100 uCi per ml of [$^{35}$S)cysteine overnight. Total cellular lysates were then reacted with patient antiserum 38-1. Cold Raji lysates were used as competitor to reduce background during immunoprecipitation. Lanes 1-4 show immunoprecipitation of untransfected Raji cells, cells transfected with pΔ(83-5365/8053-929), pΔ(83-5365/6617198/8053-9296) and pΔ[83-5365/5607-7719/8053-9296) respectively (See FIG. 6E). Immunoprecipitation of cells transiently transfected with this plasmid reveals a smaller protein of approximately 12 kD, a shift in size consistent with the expected loss of 17 amino acids.

This 14 kD protein is present in all cells tested that demonstrate trans-activation of HTLV-III/LAV LTR directed gene expression. The protein is also expressed in cell lines that contain plasmids constructed so as to express specifically proteins encoded by the tat$_{II}$ gene. These cells contain portions of the HTLV-III/LAV genome in which the entire gag, pol, sor and 3'ORF genes have been deleted. Finally, the 14 kD protein is present in cells containing the HTLV-III/LAV genome that carries substantial deletions in the env gene as well. Truncation of the tat$_{III}$ gene results in a more rapidly migrating protein. Although the immunoprecipitated protein is somewhat larger than its predicted size (10 kD), this may be due to post-translational modification, or alternatively, to anomalous migration associated with highly basic and proline-rich polypeptides.

The use of this protein can dramatically increase the rate of transcription of a heterologous gene product and hence the expression of the desired gene product.

The present invention is further illustrated by the following examples. These examples are provided to aid in understanding of the invention and are not to be construed as a limitation thereof.

EXAMPLE 1

Construction of Vector Used to Establish Tat$_{III}$ Cell Lines

The defective retroviral vector pZIPNEOSV(X) developed by Mulligan and coworkers (Cepko, et al., supra 1984) was used to construct a vector for establishing stable tat$_{III}$ cell lines. This vector contains Moloney murine leukemia virus LTRs, polyadenylation signals, sequences required for reverse transcription and for encapsidation of RNA as well as the 3' and 5' splicing signals that normally produce subgenomic RNA. In addition, the vector contains the bacterial neomycin (neo) resistance gene that confers a dominant selectable resistance to the antibiotic G418 in eukaryotic cells (Southern and Berg, supra 1982). The tat gene of HTLV-III was isolated from the plasmid shown in FIG. 1 by cleaving the DNA at the indicated restriction sites. The HTLV-III/LAC $tat_{III}$ gene was obtained from infectious proviral clone HXBC2 and encodes the HTLV-III/LAV associated trans-acting factor (See FIG. 1) (Arya et al., Science 229:69-73 (1985); Sodroski et al., Science 229:74-77 (1985)).

EXAMPLE 2

Transfection of Cell Line with $Tat_{III}$ Vector

DNA was introduced into the psi/2 (ecotropic) and psi AM (amphotropic) cell lines by the calcium phosphate coprecipitation method (Wigler et al., Cell 16:777-785 (1979). These lines constitutively produce the murine leukemia virus proteins but cannot package the viral transcripts (Cone, at el., PNAS 81: 6349-6353 (1984); Mann, et al., Cell 33:153-159 (1983)). Two days following transfection, cells were selected with the antibiotic G418 (400 µg/ml for fibroblast lines and 700 µg/ml for lymphocytes). G418 resistant clones were evident in 7 to 10 days. Insertion of the $tat_{III}$ regions did not interfere with splicing events required for transcription of the neo genes. G418-resistant psi 2 and psi AM clones were isolated and the virus from clones producing greater than $10^3$ infectious units per ml were used to infect the test cells. (King et al., Science 228:554-558 (1985)). Cells resistance to G418 were observed subsequent to infection of all the cell lines tested.

- EXAMPLE 3

Construction of Tat-$_{III}$ Fusion Product

Construction of a $tat_{III}$ fusion product in a bacterial open reading frame vector is shown in FIG. 5. About 221 nucleotides of the first coding exon of $tat_{III}$ (nucleotide 5391 to 5611) were inserted into the Sma I site of pORF1 (6) [Ratner et. al., Nature 313:227 (1985)]. Shown below are the frames of the ompF gene, the $tat_{III}$ gene and the lacZ gene. Plasmids were initially selected in E. coli strain MH3000 by scoring for blue lacZ+ colonies on LB-ampicillin plates containing 5-bromo-4-chloro-3-indoxyl-beta-D-gal Ratner et. al, supra]. Plasmids were then transferred to E. coli TK1046, a strain that permits higher expression of the ompF promoter.

EXAMPLE 4

Expression of $Tat_{III}$ Product

Expression of the fusion ompF-$tat_{III}$-betagalactosidase protein is shown in FIG. 6A. Tk1046 cells containing pBGT-III or pBG were grown in L broth at room temperature until the optical density at 550nm was approximately 0.3 to 0.4. They were then labelled in M63 glucose medium with 100uCi of [$^{35}$S]cysteine per ml for 15 minutes. Labeled proteins were processed for immunoprecipitation as previously described (6) [G. Weinstock, et. al., PNAS 80:4432 (1983)]. Lanes 1-6 are immunoprecipitates of the ompF-betagalactosidase product from pBG with rabbit anti-beta-galactosidase serum, patient anti-serum 4-3, 11-2, 12-4, 13-4 and 38-1 respectively. Lanes 7-are immunoprecipitates of the ompF-$tat_{III}$-betagalactosidase protein from pBGT-III with rabbit anti-beta-galactosidase serum, patient serum 4-3, 11-2, 12-4, 13-4 and 38-1 respectively (k=kDa)

EXAMPLE 5

Deletion analysis (a) Structure of HTLV-III/LAV deletion mutants that retain trans-activating ability is shown in FIG. 5. The restriction map of the complete HTLV-III/LAV provirus in plasmid pHXBc2 is shown on the topmost line. The second line drawing depicts the splicing pattern of the message coding for the potential $tat_{III}$ gene product based on the sequence of cDNA messages from HTLV-III/LAV infected cells ([Sodroski et al., Science 227, Supra; Sodroski et al., ibid 119, supra; Arya et al., supra; Mussing et al., Nature 313:450 ([1985]) Construction of the deletion mutants is described below. Numbers corresponding to the deletion endpoints are based on the sequence of Ratner et al. supra where the RNA cap site is designated as +1. Zigzag lines mark the polyadenylation and splice signals from the SV40 small t-antigen coding region (H=Hind III; S=Sal; Bg=Bg1/II; Bm=Bam HI).

(b) To construct the deletion DNAs plasmid pU3R-I$^7$ was first cleaved at the unique site Sma I site (position -322) within the LTR. Digested DNA was incubated with the exonuclease Bal 31. At various time points aliquots were removed and the DNA was phenol chloroform extracted then ethanol precipitated. Any protruding ends were filled with T4 polymerase followed by ligation to Xho I linkers. After linker addition the DNA was recircularized and transfected into E. coli strain HB101. Several size selected clones were characterized by restriction enzyme analysis. The desired clones were then end labeled at the Xho I site and subjected to Maxam and Gilbert sequence analysis (see Maxam, A. M. et. al., Proc. Natl. Acad. Sci. USA. 74: 560-564 (1977)) to determine the end points. The name of each plasmid is indicative of the number of nucleotides present relative to the transcription start site.

(c) The deletion DNAs were transfected into the following cell types by a modification of the DEAE dextran coprecipitation technique (see Queen C. et al., Cell, 33: 729 (1983)). Hela, a epithelial cell line; HUT 78, an OKT4+ helper/inducer human T cell line derived from an HTLV negative patient with sezary syndrome (see Gey, et al., Cancer Res., 12: 264 (1952)); NC37, a B lymphocyte line established from a normal donor and immortalized by Epstein Barr virus (see Manzari, V. et al., Proc. Nat. Acad. Sci. USA. 80: 11-15 (1983)); and C81-66/45, derived by fusion of primary umbilical cord blood cells with an HTLV-I producing cell line (see Salahuddin, S. Z. et al., Virology, 129: 51-64 (1983)). This cell line does not produce virus but contains the HTLV-I associated trans-acting factor. Forty eight hours following transfection cellular extracts were made and CAT assays were performed as described. The values shown are normalized to the CAT activity present in similar cells transfected with a control plasmid pSV2CAT taken as 1.0. The bracketed number indicates the relative CAT activity in infected cells compared with uninfected cells normalized to the activity present in the uninfected lymphocyte lines transfected with the pSV2CAT plasmid that contains the SV40 enhancer promoter sequences (Laimins et al., supra).

TABLE 2

Effect of HTLV III/LAV tat gene expression on HTLV III-LAV LTR directed gene expression.

| Cell lines[a] | Plasmids[b] Relative CAT Activity[c] | |
|---|---|---|
| | pSV2CAT | pU3R-III |
| Hela | 1.0 | .10 |
| Hela III extat | 1.0 | 67 (670) |
| Raji | 1.0 | .24 |
| Raji ZIONEOtat$_{III}$ | 1.0 | 650 (2708) |
| HUT 78 | 1.0 | .60 |
| HUT/78ZIPNEO/tat$_{III}$ | 1.0 | 330 (550) |

[a] The Raji ZIPNEO tat$_{III}$ and HUT78 ZIPNEO tat$_{III}$ cell lines were established by infection with the retroviral tat$_{III}$ expression vector pZIPNEO tat$_{III}$ as previously described. the Hela III-extat line was established via cotransfection with plasmids III-extat (formerly pΔ83-5365/8053-9296) and pU3R-IIINEO)

[b] Plasmid pSV2CAT contain the bacterial chloramphenicol acetyltransferase (CAT) gene under control of the SV40 early region promoter sequences C. Gorman, Moffat, L. F. and Howard, B. Mol. Cell. Biol. 2, 1044 (1982). Plasmid pU3R-III contain HTLV-III/LAV LTR sequences directing expression of the CAT gene.

[c] Cells were transfected with 2 ng of plasmid DNA and CAT assays were performed 48 hours post-transfection. The CAT activity is normalized to the activity obtained with pSV2CAT in the same cell. The number in parenthesis represents the fold stimulation in the infected as compared to the uninfected cells.

The present invention permits high levels of production of proteins and like-materials expressable by genes.

Figure 8:
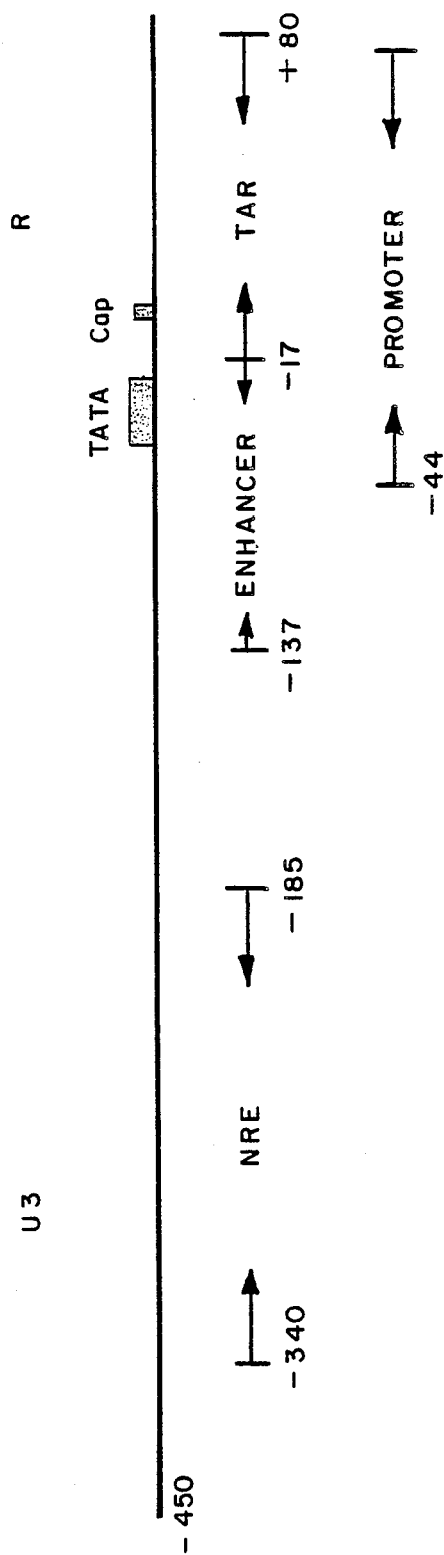
FIG. 8 represents a portion of the HTLV-III LTR containing regulatory regions.

There are genetic segments of the HTLV-III LTR region which in the presence of the tat$_{III}$ gene product, result in high rates of gene expression. These segments are called TAR elements and can be utilized to provide a trans-activated response. The location of this TAR element has been mapped to lie between nucleotides −17 and +80 of the HTLV-III genome as shown in FIG. 8 [Rosen, C. A. et al., Cell 41:813–823 (1985)). However, when only this portion of nucleotide segment is used, it must be provided with another enhancer upstream to provide trans-activation for the tat$_{III}$ product. More preferably, the nucleotide region ranging from −167 through +80 is used. This nucleotide region contains an enhancer sequence, between −137 and −17.

By using a vector containing a TAR sequence, and a desired heterologous gene and transfecting the tat$_{III}$ cell lines of the present invention, it will be possible to result in trans-activating the tat$_{III}$ cell line, thereby producing high yields of the desired heterologous gene product. Alternatively, use of the the tat$_{III}$ protein of the present invention can be trigger trans-activation, thereby achieving high levels of expression of the desired gene product. This can be accomplished by adding the tat$_{III}$ protein to a culture medium, wherein a cell has been transfected with a predetermined heterologous gene and a TAR element.

One can use a vector containing only the TAR element and a tissue specific enhancer to result in transactivating only specific cells. For example, one could use the enhancer for the immunoglobulin gene to result in activating only B lymphocyte cells.

The present invention also permits the use of an improved process for detecting the presence of HTLV-III/LAV virus in individuals. Current assay techniques require culturing lymphocytes from individuals. This is a time consuming and costly process. In addition, the sensitivity of current assay techniques will not always detect the presence of the virus.

We have discovered that by using the tat$_{III}$ cell lines of the present invention, a sensitive and efficient assay method is possible. Preferably, one takes lymphocytes or whole blood and adds it to a culture medium containing the tat$_{III}$ cell lines of the present invention, but other "fluid" can be used. More preferably one uses lymphocytes. These cells are then incubated at 37° C. and watched to determine whether or not a cytopathic effect is exhibited in the tat$_{III}$ cell line.

Preferably, one uses a tat$_{III}$ cell line established from a cell line that is particularly sensitive to the cytological property of the HTLV-III/LAV virus. Such cell lines include HUT 78 cells, C8161 cells and Jurkat cells.

Preferably, the cell lines contain that is released upon the cell's death. This marker can be used to determine the cytopathic effect of the tested material. Thus, when a cell dies, the marker is released into the culture medium resulting in a reaction with the medium that is visually observed. Examples of such markers include chromium.

This assay system allows for the detection of the HTLV-III/LAV virus in periods of time typically as short as three days as opposed to the normal two weeks that it takes with using reverse-transcriptase. Cultivation and incubation techniques used are those well known to anybody of ordinary skill in the art.

The tat$_{III}$ cell lines of the present invention also permit the development of a system for screening for a compound that will mitigate the cytopathic effects of the HTLV-III/LAV virus. Using these tat$_{III}$ cell lines, two types of transfected cell lines are created to detect the differential response of the cells. In both types, the cell is transfected with a vector containing a heterologous gene, whose gene product is selectable for example, the CAT gene. In the first situation, the expression of the heterologous gene product is under the control of an HTLV-III TAR element, more preferably the full HTLV-III LTR, and thus the level of its expression is effected by the functioning of the tat$_{III}$ gene product. In the second cell line, the heterologous gene is under the control of a separate regulatory sequence, and the level of expression of the selectable gene product is independent of tat$_{III}$ function. Thereafter, a compound to be screened is added to each cell type by standard techniques in increasing concentrations. The expression of the selectable gene is measured by techniques well known in the art to determine which compounds inhibit tat$_{III}$ function without being toxic to the cell itself.

It is preferable to screen compounds that prevent the interaction of the tat$_{III}$ protein with the sequences responsive to the tat$_{III}$ protein in the HTLV-III LTR or prevent the ability of the tat$_{III}$ protein to trans-activate the HTLV-III LTR.

We have found that in cell lines, exhibiting trans-activation by the tat$_{III}$ protein and thus, high levels of protein expression, there is a negligible increase in the levels of corresponding messenger RNA. Consequently, using compounds that inhibit translation, such as substances that affect the formation of translational initiation complexes or alter the bonding of ribosomes to the viral mRNA is most preferable.

Examples of compounds that can be used in this screening process include competitors, compounds that inhibit translation and compounds that alter the binding ability of a compound. Compounds such as those described in the *Physicians' Desk Reference*, 38th ed. Medical Economics Co., Droden, N.J. (1984), that can be used in the present screening process can be readily determined by the person of ordinary skill in the art based upon the above disclosure.

A preferred group of competitors would be mutant tat$_{III}$ proteins that would retain their ability to bind to nucleic acid but are deficient in some other trans-activation function. Such proteins should serve as efficient competitors for functional $tat_{III}$ proteins. Random mutagenesis by, for example, chemical modification can be used to generate large numbers of $tat_{III}$ mutants without a specified target region. In one embodiment, one would use the first coding exon of $tat_{III}$ which can be isolated using convenient restriction endonuclease sites. This region will be cloned into the replicative form of phage M13.

Single stranded M13 containing the $tat_{III}$ insert in either orientation is mutagenized using methoxyalamine. This can generate single and double nucleotide substitutions at a frequency of greater than 50% [(Kadonaga and Knowles, *Nucl. Acids Res.,* 13:1733 (1985). The single stranded DNA of a clone in one orientation is annealed to that of a clone in another orientation so that a double stranded insert is reconstituted. The chemically modified inserts are removed from vector M13 DNA by restriction digestion and recloned into cut alkaline-phosphatase treated M13 replicative form DNA. Clones containing inserts are identified by the colorless plaques generated when the insert disrupts the beta-galactosidase gene present in the M13 vector. The insert fragment can then be sequenced using the dideoxy method of Sanger et al., *PNAS,* 74:5463 (1977).

Following generation and sequencing of $tat_{III}$ mutants in M13 by the methods described above, the insert fragments are recloned into an HTLV-III expression vector containing HTLV-III LTR and a selectable heterologous gene, such as CAT and transfected into eukaryotic cells. The activity of the mutant $tat_{III}$ proteins will be determined by testing their ability to trans-activate the HTLV-III LTR in a co-transfection assays. Using the transient CAT assays as many as 100 plasmid clones can be tested for activity in the period of one week. Moreover, mutations that increase or decrease the trans-activating ability can be detected in a quantitative manner.

Those mutants that are no longer able to trans-activate will be tested in the above-described screening process. If a mutant $tat_{III}$ protein that can effectively compete with the active form is found then the mutant $tat_{III}$ gene will be subcloned into the retroviral vector.

The $III_{III}$ protein of the present invention can also be used to develop anti-sera which could effectively block infection by HTLV-III/LAV virus. We have found that a fusion protein containing this protein is immunoreactive with patient serum (See FIG. 6). The protein is used as an immunogen for raising polyclonal and monospecific antibodies $tat_{III}$ protein of the present invention can be used to immunize rabbits or goats either as pure protein or a betagalactosidase fusion product (See FIGS. 5 and 6).

The effectiveness of the anti-sera can be tested by techniques well known to the person of ordinary skill in the art. For example the $tat_{III}$ anti-sera (or purified IgG fraction) together with the appropriate plasmids is injected into Xenopus oocytes. The HTLV-III LTR transcriptional regulatory sequences direct high levels of CAT gene expression in this system and because oocytes synthesize large quantities of RNA and protein following microinjection this system is better suited than microinjection into cells.

The $tat_{III}$ anti-sera is introduced into the oocytes together with the pU3R-III plasmid (HTLV-III LTR upstream of CAT) and several different $tat_{III}$ gene expressor plasmids. Control experiments using plasmids unresponsive to $tat_{III}$ and normal serum will be done in parallel in an analogous manner to the screening process described above. A decreased level of CAT gene expression directed by plasmid pU3R-III and the $tat_{III}$ expressor plasmid in the presence of the $tat_{III}$ specific anti-sera indicates inhibition of trans-activation.

It is evident that those skilled in the art, given the benefit of the foregoing disclosure, may make numerous other uses and modifications thereof, and departures from the specific embodiments described herein without departing from the inventive concepts, and the present invention is to be limited solely by the scope and spirit of the appended claims.

We claim:

1. A method for enhanced expression of heterologous DNA comprising:

(a) transfecting a cell with (1) a vector containing a sufficient portion of an HTLV-III $tat_{III}$ gene to produce a $tat_{III}$ gene product which acts as a trans-activator on an HTLV-III LTR or fragment thereof, (2) a second vector containing a sufficient amount of an HTLV-III LTR which is capable of responding to the $tat_{III}$ gene product, and an enhancer upstream of said LTR or functional fragment thereof and the heterologous DNA downstream of the LTR or fragment thereof; and (b) culturing the co-transferred cell.

2. The method of claim 1, wherein the product of the heterologous DNA is recovered.

3. The method of claim 1, wherein the LTR is the 5′ LTR or functional fragment thereof.

4. A method for producing a stable cell line containing the tat III gene which comprises:

(a) transfecting a preselected cell with a vector containing a tat III gene but not the complete HTLV-III/LAV genome, and (b) culturing the transfected cells.

5. A stable cell line containing the $tat_{III}$ gene, but not the complete HTLV-III/LAV genome.

6. The method of claim 1 wherein the sufficient amount is at least from nucleotides −17 through +80 of the HTLV-III LTR.

7. The method of claim 1, wherein the sufficient amount is the HTLV-III TAR element.

8. The method of claim 1 wherein the sufficient amount is at least from nucleotides −167 through +80 of the HTLV-III LTR.

9. The method of claim 8 wherein the viral enhancer is part of the HTLV-III LTR.

10. The method of claim 1 wherein the heterologous DNA is the gene coding for chloraphenicol acetyltransferase.

11. The $tat_{III}$cell line of claim 5 wherein the cell line is a Raji cell line.

12. The $tat_{III}$cell line of claim 5 where the cell line is a HeLa cell line.

13. The $tat_{III}$cell line of claim 5 where the cell line is a NIH $3T_3$ cell line.

14. The $tat_{III}$cell line of claim 5 where the cell line is a Jurkat cell line.

15. The $tat_{III}$cell line of claim 5 where the cell line is a human T-cell line.

16. The $tat_{III}$cell line of claim 5 where the cell line is a human B-cell line.

* * * * *